US009974825B2

(12) United States Patent
Souza dos Santos et al.

(10) Patent No.: US 9,974,825 B2
(45) Date of Patent: May 22, 2018

(54) PEPTIDES DES-[ASP¹]-[ALA¹], ANGIOTENSIN-(1-7) AGONIST AND PHARMACEUTICAL COMPOSITIONS FOR THE TREATMENT OF DISEASES

(75) Inventors: Robson Augusto Souza dos Santos, Belo Horizonte (BR); Anderson José Ferreira, Belo Horizonte (BR); Rubén Dario Sinisterra, Belo Horizonte (BR); Rodrigo Araújo Fraga da Silva, Belo Horizonte (BR); Roberto Queiroga Lautner, Belo Horizonte (BR)

(73) Assignee: UNIVERSIDADE FEDERAL DE MINAS GERAIS, Belo Horizonte (BR)

( * ) Notice: Subject to any disclaimer, the term of this patent is extended or adjusted under 35 U.S.C. 154(b) by 1263 days.

(21) Appl. No.: 12/867,599

(22) PCT Filed: Feb. 13, 2009

(86) PCT No.: PCT/BR2009/000046
§ 371 (c)(1),
(2), (4) Date: Apr. 18, 2011

(87) PCT Pub. No.: WO2009/100513
PCT Pub. Date: Aug. 20, 2009

(65) Prior Publication Data
US 2013/0183367 A1 Jul. 18, 2013

(30) Foreign Application Priority Data
Feb. 13, 2008 (BR) ...................................... 0800585

(51) Int. Cl.
*A61K 38/08* (2006.01)
*C07K 7/14* (2006.01)

(52) U.S. Cl.
CPC .............. *A61K 38/085* (2013.01); *C07K 7/14* (2013.01)

(58) Field of Classification Search
CPC ................................ A61K 38/085; C07K 7/14
See application file for complete search history.

(56) References Cited

U.S. PATENT DOCUMENTS

| | | | | |
|---|---|---|---|---|
| 6,110,895 A * | 8/2000 | Rodgers | ................... | C07K 7/14 514/9.7 |
| 2003/0017989 A1 * | 1/2003 | Sim | ..................... | A61K 38/085 514/16.4 |
| 2003/0086920 A1 * | 5/2003 | Sim | ..................... | A61K 38/085 424/94.64 |
| 2003/0203834 A1 * | 10/2003 | Tallant | ................. | A61K 38/085 514/1 |
| 2004/0171584 A1 | 9/2004 | Millan et al. | | |
| 2005/0119180 A1 * | 6/2005 | Roks | .................... | A61K 38/085 514/16.2 |
| 2008/0108575 A1 | 5/2008 | Millan et al. | | |
| 2008/0249015 A1 * | 10/2008 | Sim | ...................... | A61K 38/085 514/1.1 |
| 2008/0312129 A1 | 12/2008 | Santos et al. | | |
| 2009/0221498 A1 | 9/2009 | Santos et al. | | |
| 2010/0144624 A1 | 6/2010 | Millan et al. | | |
| 2010/0196452 A1 | 8/2010 | Santos et al. | | |

FOREIGN PATENT DOCUMENTS

WO    WO 03/039434    *    5/2003
WO    2009/100513 A3    11/2009

OTHER PUBLICATIONS

Yin et al., Journal of Biotechnology (2007) 127, 335-347.*
Vauquelin et al., 2002, Cellular targets for angiotensin II fragments: pharmacological and molecular evidence, Journal of the Renin-Angiotensin-Aldosterone System, 3(4): 195-204.*
Moeller et al., 1998, Bioactive angiotensin peptides, Journal of Human Hypertension, 12: 289-293.*
Terui et al., 1994, Proteinuric Potentials of Angiotensin II, [des-Asp1]-Angiotensin II, and [des-Asp1, des-Arg2]-angiotensin II in Rats , Biol Pharm Bull, 17(11): 1516-1518.*
Sim et al., 1998, Effects of des-Asp-angiotensin I on experimentally-induced cardiac hypertrophy in rats, Internationl Journal of Cardiology, 63: 223-227.*
Coleman et al., 1998, Changes in cochlear blood flow due to intra-arterial infusions of angiotensin II (3-8) (angiotensin IV) in guinea pigs, Hearing Research, 119: 61-68.*
Tan et al., 2000, Actions of Angiotensin Peptides on the Rabbit Pulmonary Artery, Life Sciences, 66(19): 1839-1847.*
Chen et al., 2002, Structure-activity and structure-binding studies of des-Asp1-angiotensin I analogues on the rabbit pulmonary artery, Regulatory Peptides, 106: 39-46.*
Villela et al., 2014, Alamandine: a new member of the angiotensin family, Curr Opin Nephrol hypertens, 23(2): 130-134.*
Pu et al., 2005, Family of multiple peptide fragments derived from angiotensin and their interaction, Journal of Peking University (Health Sciences), 37(6): 661-665.*
Campbell et al., 1976, organ Specificity of Angiotensin II and Des-aspartyl Angiotensin II in the Conscious Rat, the Journal of Pharmacology and Experimental Therapeutics, 198(2): 450-456.*
Sarstedt et al., 1975, Selective Inhibition by des-1-Asp-8-Ile-Angiotensin II of the Steroidogenic Response to Restricted Sodium Intake in the Rat, Circulation Research, 37: 350-358.*
Ackerly et al., 1977, Demonstration of different contractile mechanisms for angiotensin II and des-Asp1-angiotensin II in rabbit aortic strips, PNAS, 74(12): 5725-5728.*
Freeman et al., 1976, Evidence that Des-Asp1-angiotensin II Mediates the Renin-Angiotensin Response, Circ Res, 38(6 suppl 2): 99-103.*
Lim et al., 1998, Actions of Des-Asp-Angiotensin I on the Aortic Rings of the Normo- and hypertensive Rats, Clin and Exper Hypertension, 20(1): 105-117.*

(Continued)

*Primary Examiner* — Amber D Steele
(74) *Attorney, Agent, or Firm* — Nixon & Vanderhye PC

(57) ABSTRACT

The present invention is related to the peptide Des-[Asp¹]-[Ala¹]-Angiotensin-(1-7) (Ala¹-Arg²-Val³-Tyr⁴-Ile⁵-His⁶-Pro⁷) (SEQ ID NO: 1) and/or its related compounds as vasodilating and cardioprotective agents to be used in mammals. This invention also comprises the production of compounds containing Des-[Asp¹]-[Ala¹]-Angiotensin-(1-7) and/or its related compounds and its use in methods for treating and preventing diseases.

19 Claims, 3 Drawing Sheets

(56) References Cited

OTHER PUBLICATIONS

Spielman et al., 1976, Des-Asp-1-Angiotensin II: Possible Role in Mediating the Renin-Angiotensin Response in the Rat, Proc Soc Exp Biol Med, 151(1): 177-182.*

Ohishi et al., 2013, Angiotensin (1-7) and other Angiotensin Peptides, Current Pharmaceutical Design, 19: 3060-3064.*

Min et al., 2000, Effects of des-aspartate-angiotensin I on angiotensin II-induced incorporation of phenylalanine and thymidine in cultured rat cardiomyocytes and aortic smooth muscle cells, Regulatory Peptides, 95: 93-97.*

Jankowski et al. "Mass-spectrometric identification of a novel angiotensin peptide in human plasma" *Arterioscler Thromb Vasc Biol*, vol. 27, No. 2, pp. 297-302 (Feb. 2007).

Santos et al. "Angiotensin-(1-7) is an endogenous ligand for the G protein-coupled receptor Mas" *Proc Natl Acad Sci USA*, vol. 100, No. 14, pp. 8258-8263 (Jul. 2003).

Int'l Search Report for PCT/BR2009/000046, all five pages (Jul. 2009).

Written Opinion for PCT/BR2009/000046, all four pages (Jul. 2009).

* cited by examiner

PEPTIDES DES-[ASP$^1$]-[ALA$^1$], ANGIOTENSIN-(1-7) AGONIST AND PHARMACEUTICAL COMPOSITIONS FOR THE TREATMENT OF DISEASES

This application is the U.S. national phase under 35 U.S.C. 371 of Int'l Application No. PCT/BR2009/000046, filed 13 Feb. 2009, which designated the U.S. and claims priority to Brazilian Application No. PI0800585-0, filed 13 Feb. 2008; the entire contents of each of which are hereby incorporated by reference.

The present invention refers to PEPTIDE Des-[Asp$^1$]-[Ala$^1$], Angiotensin-(1-7) (Ala$^1$-Arg$^2$-Val$^3$-Tyr$^4$-Ile$^5$-His$^6$-Pro$^7$) agonist and its related pharmaceutical compositions to be used, for example, as vasculoprotective and cardioprotective agents in mammals. The invention encompasses compositions containing the PEPTIDE Des-[Asp$^1$]-[Ala$^1$]-Angiotensin-(1-7) or its related compounds. And it also refers to methods for treating or preventing diseases or disorders, which consists in delivering the PEPTIDE Des-[Asp$^1$]-[Ala$^1$]-Angiotensin-(1-7) and/or its related compounds to patients. Such diseases or disorders include, for example, vascular or cardiovascular diseases as primary or secondary hypertension, vascular-renal hypertension, atherosclerosis, ischemic and reperfusion injury, acute myocardial infarction, acute or chronic congestive myocardial insufficiency, left ventricular hypertrophy, vascular hypertrophy, primary and secondary hyperaldosteronism, diabetes, neuropathic diabetes, glomerulonephritis, scleroderma, glomerular sclerosis, renal insufficiency, therapies in organ transplantation, diabetic retinopathy, nephropathies, angioplasties and erectile dysfunction.

The vasoactive octaPEPTIDE angiotensin II (Ang II), which is considered as the major active member of the renin-angiotensin system (RAS), plays a crucial role in the cardiovascular regulation physiology and pathophysiology. The therapeutic success of the inhibitors of the angiotensinogen converting enzyme (ACE) and that of receptor AT$_1$ blockers, as vasculoprotectors and cardioprotectors, refers to the important role of Ang II in atherosclerosis and hypertension pathophysiology. Other less characterized PEPTIDES in the angiotensin family include angiotensin III, angiotensin IV and angiotensin-(1-7) [Ang-(1-7)]. These PEPTIDEs have additional or antagonic effects to those of Ang II. Angiotensin IV is an agonist of receptor AT$_4$ and produces vasodilating action and inhibits cellular proliferation. Ang-(1-7) frequently shows opposite actions to those attributed to Ang II, such as vasodilation, anti-arrhythmogenic effect and inhibition of cellular proliferation and is currently considered as the major counter regulator of Ang II cardiovascular effects. Recently, a receptor coupled with proteins G has been identified as being the receptor for Ang-(1-7).

G protein coupled receptors (GPCRs) present seven sequences from 22 to 24 residues of hydrophobic amino acids that form seven transmembrane α-helices. These transmembrane helices are connected by loops composed of hydrophilic amino acid residues, the larger loop being located between the fourth and fifth helices in the extracellular portion. Another large loop connects helices five and six in the intracellular portion. The receptor's carboxy-terminal portion is located in the intracellular region and the amino-terminal, in the extracellular portion. It is well-known that the loop between helices five as well as the carboxy-terminal portion are the regions responsible for the interaction between the receptor and protein G. Nowadays, proteins G are identified as Gq, Gs, Gi and Go.

In physiological conditions, GPCRs remain in equilibrium in the cellular membrane in two different states or conformations: inactivated or activated states. An inactivated receptor becomes unable to promote intracellular signal transduction and in this way produce a biological response. When the conformation of the receptor, activating it, the receptor promotes intracellular signal transduction producing a biological response. Physiologically, this conformation change is induced by the interaction of a molecule with the receptor. Different kinds of biological molecules may bind to specific receptors, e.g., PEPTIDES, hormones and lipids and thus promote a cellular response. Modulation of specific cellular response is of great interest for treating diseases and several chemical agents act in GPCRs in the treatment of various diseases.

The Mas protooncogen, which codifies the GPCR protein (Mas), was first detected in vivo due to its tumorigenic properties that were originated from rearrangements in the 5' flanking region. (Young, D. et al., Cell 45:711-719 (1996)). Subsequent studies suggested that Mas tumorigenic properties seemed to be insignificant.

It was first believed that Ang II was the ligand for the Mas receptor (Jackson et al., Nature 335:437-440 (1988)). However, it was later determined that intracellular responses to calcium in transfected cells containing the Mas receptor have only occurred in cells coexpressing the Ang II receptor (Ambroz et al. Biochem. Biophys. Acta 1133:107-111 (1991)). Other experiments have shown a possible role for Mas receptor in modulating intracellular signaling of Ang II receptors after stimulation by Ang II (von Bohlen and Halbech et al., J. Neurophysiol. 83:2012-2020 (2000)). Furthermore, Dong et al. reported that both Angiotensin I (Ang I) and Ang II have not shown ligand affinity with Mas receptor, except for one PEPTIDE called NPFF, which had shown affinity with the receptor, though reasonably feeble (EC50 about 400 nM) (Dong et al., Cell 106:619-632 (2001)).

Recently, it was demonstrated that Ang-(1-7) (Asp$^1$-Arg$^2$-Val$^3$-Tyr$^4$-Ile$^5$-His$^6$-Pro$^7$) is a high-affinity ligand with Mas receptor (Kd=0.33 nM) (Santos, R. A. S. et o al., PNAS 100:8258-8263 (2003)), which might point to a possible role for the Mas receptor in regulating blood pressure and production of thrombo.

RAS consists in a series of enzymatic reactions that end up in the generation of Ang II in plasma and various tissues, including those of heart and kidneys. After being released by juxtaglomerular cells in afferent renal arterioles, the renin enzyme generates the inactive Ang I decaPEPTIDE by breaking the angiotensinogen, which is synthesized and released by the liver (Hackenthal E., et al. Physiol. Rev. 70:1067-1116 (1990), Tanimoto k., et al. J. Biol. Chem. 269:31,334-31,337 (1994)). The peptidase action of angiotensin converting enzyme (ACE) converts Ang I into the octaPEPTIDE Ang II. Two ACE isoforms have been described: (i) somatic ACE, containing two homologous domains from the gene duplication within a repetition, each with a functional catalytic site; and (ii) testicular ACE, containing just one C-terminal domain as catalytic site (Turner A. J., and Hooper N. M., Trends. Pharmacol. Sci. 23:177-183 (2002)). Far from the Renin-Angiotensin System (RAS) classical viewpoint, new features have been discovered recently, which reveal the complexity of this system.

Firstly, tissue Ang II may be generated form enzymes nonrelated to ACE (Wei C. C., et al. Am. J. Physiol. Heart. Circ. Physiol. 282:H2254-2258 (2002)). A further feature is that ACE may cleave and inactivate other PEPTIDES, such as bradykinin and kallidin, which are potent vasodilators that offset Ang H effects (Turner A. J., and Hooper N. M., Trends. Pharmacol. Sci. 23:177-183 (2002)). A new enzyme was recently discovered—a component of RAS, ACE2—that is able to metabolize several PEPTIDES of RAS (Donoghue et al. Circ. Res. 87:E1-E9 (2000). ACE 2 may cleave Ang I (in the C-terminal portion) and generate the inactive PEPTIDE Ang-(1-9), which can be later converted into the vasodilator PEPTIDE Ang-(1-7) by ACE or other peptidases (Donoghue et al. Circ. Res. 87:E1-E9 (2000). More importantly, ACE2 can directly cleave Ang II (in the C-terminal portion) generating Ang-(1-7).

The cardiovascular and baroreflex actions provoked by Ang-(1-7) are said to be contra-regulatory in relation to Ang II actions. However, Ang II once acting through receptor AT1 causes vasoconstriction and a simultaneous increase in blood pressure and Ang-(1-7) via Mas receptor promotes vasodilation and thus makes blood pressure to decrease (Santos, R. A. S. et al., Regul. Pept. 91:45-62 (2000)).

It has been shown that Ang-(1-7) has vasodilating effect on several vascular beds, including coronary arteries of dogs and pigs, aorta of rats and feline mesenteric artery. It has also been demonstrated that a chronic infusion of Ang-(1-7) leads to a reduced mean arterial pressure in spontaneously hypertensive rats and Dahl rats sensitive to salt. Other studies have shown Ang-(1-7) may block vasoconstriction provoked by Ang II in isolated human arteries as well as Ang II antagonized vasoconstriction in circulation of normotensive humans. Direct vasodilation caused by Ang-(1-7) in the same extent to basal circulation has been observed in both normotensive and hypertensive patients. Although its mechanism is still undefined, it has been verified that the vasodilating effect of bradykinin is potentiated by Ang-(1-7).

Several actions of Ang-(1-7) are antagonized by the selective antagonist of the Ang-(1-7) (Asp$^1$-Arg$^2$-Val$^3$-Tyr$^4$-Ile$^5$-His$^6$-D-Ala$^7$) (A-779) receptor, which acts as an antagonist of the Mas receptor. Nevertheless, some effects caused by Ang-(1-7) are only partially reverted by A-779 (Silva, D. M. R. et al., Peptides 28:702-707 (2007). Additionally, several studies have demonstrated that Ang-(1-7) may interact with ACE, AT$_1$ and with receptors related to the AT$_2$ receptor, which suggests the existence of other interaction sites for Ang-(1-7).

Recently, studies carried out in our laboratory have pointed to a possible new subtype of the receptor for Ang-(1-7), since vasodilation caused by Ang-(1-7) in aorta of Sprague-Dawley rats was blocked by the Mas receptor, D-pro7-Ang-(1-7) (Asp$^1$-Arg$^2$-Val$^3$-Tyr$^4$-Ile$^5$-His$^6$-D-Pro$^7$), though it was not blocked by A-779 (Silva, D. M. R. et al., Peptides 28:702-707 (2007).

Recent works have demonstrated that Ang II can be processed into Des-[Asp$^1$]-[Ala$^1$]-Angiotensin II (Ala$^1$-Ang II) by post-translational decarboxylation of the aspartic amino acid residue into alanine. The affinity of the Ala$^1$-Ang II with AT$_1$ or AT$_2$ receptor does not substantially differ from Ang II. However, the pressor activity of Ala$^1$-Ang II in wild-type mice is only a fraction of the Ang II activity (Jankowski, V. et al., Arterioscler. Thromb. Vasc. Biol. 27:297-302 (2007)). PEPTIDE Des-[Asp$^1$]-[Ala$^1$]-Angiotensin-(1-7) (Ala$^1$-Arg$^2$-Val$^3$-Tyr$^4$-Ile$^5$-His$^6$-Pro$^7$), a peptide processed by decarboxylation of the aspartic amino acid residue into alanine or its possible biological effects, as well as applications for treating diseases were not mentioned in this study.

Cyclodextrins belong to the family of cyclic oligosaccharides, which include six, seven or eight units of glucopyranose. Due to esteric interactions, cyclodextrins (CDs) form a truncated cone-shaped cyclic structure with an apolar internal cavity. These are chemically stable compounds, which may be modified in a regioselective way.

Cyclodextrins (hosts) form complexes containing several hydrophobic molecules (guests), including the same molecules entirely or partially in the cavity. CDs have been used for solubilization and encapsulation for drugs, perfumes and aromatizers as described by Szejtli, J., Chemical Reviews, (1998), 98, 1743-1753; Szejtli, J., I. Mater. Chem., (1997), 7, 575-587.

According to detailed studies of their toxicity, mutagenicity, teratogenicity and carcinogenicity described by Rajewski, R. A., Stella, V., J. Pharmaceutical Sciences, (1996), 85, 1142-1169, cyclodextrins have shown low toxicity, especially that of hydroxypropyl-p-cyclodextrin, as related by Szejtli, J., Cyclodextrins: Properties and applications. Drug Investig., (1990) 2(suppl. 4):11-21. Except for high concentrations of some derivatives, which provoke damages to erythrocytes, such products do not usually cause risks to health.

CDs are moderately soluble in water, methanol, ethanol and readily soluble in aprotic polar solvents, such as dimethyl sulfoxide, dimethylformamide, N,N-dimethylacetamide and pyridine.

There are numerous works in the literature about the effects of increased solubility in water of scarcely water-soluble guests by using cyclodextrins via inclusion complexes as well as a discussion on stability of inclusion complexes, whose physico-chemical features were well-described in Szejtli, J., Chemical Reviews, (1998), 98, 1743-1753. Szejtli, J., J. Mater. Chem., (1997), 7, 575-587. Cyclodextrins may be used for obtaining pharmaceutical formulations with peptides and/or proteins viewing improved stability and bioavailability.

Therefore, the present invention has used the formation of supermolecular complexes between the PEPTIDE Des-[Asp$^1$]-[Ala$^1$]-Angiotensin-(1-7) (Ala$^1$-Arg$^2$-Val$^3$-Tyr$^4$-Ile$^5$-His$^6$-Pro$^7$) and cyclodextrins, as an example of pharmaceutical composition used for treating or preventing diseases. For example, such diseases or disorders include vascular or cardiovascular diseases as primary or secondary hypertension, vascular-renal hypertension, atherosclerosis, ischemic and reperfusion injury, acute myocardial infarction, acute or chronic congestive myocardial insufficiency, left ventricular hypertrophy, vascular hypertrophy, primary and secondary hyperaldosteronism, diabetes, neuropathic diabetes, glomerulonephritis, scleroderma, glomerular sclerosis, renal insufficiency, therapies for organ transplantations, diabetic retinopathy, nephropathies, angioplasties and erectile dysfunction.

In addition to cyclodextrins, biodegradable polymers, mucoadhesive polymers and gels as well as controlled release devices of the PEPTIDE Des-[Asp$^1$]-[Ala$^1$]-Angiotensin-(1-7) are also used.

Several polymers have been tested in controlled release systems, many of them for their physical properties, as follows: poly(urethanes) for their elasticity poly(siloxanes) or silicones for being good insulations, poly(methylmethacrylate) for its physical strength, poly(vinyl alcohol) for its hydrophobicity and resistance, poly(ethylene) for its hardness and impermeability (Gilding, D. K. Biodegradable polymers. Biocompat. Clin. Implat. Mater. (1981) 2:209-232).

However, the material must be chemically inert and free from impurities for human use. Some of the materials used in release systems are as follows: poly(2-hydroxy-ethylmethacrylate), polyacrylamide, polylactic acid (PLA) based polymers, polyglycolic acid (PGA) based polymers and respective copolymers (pLGA) and the poly(anhydrides), such as polysebacic acid (PSA) based polymers and copolymers with more hydrophobic polymers.

Some patents describe the use of peptides of Angiotensin (1-7), as in the case of patent PI0105509-7 (WO03039434A2, WO03039434A3), Milián, Dos Santos et. al. (2003), which characterizes the formulation process of Angiotensin-(1-7) peptide and its analogues, agonists and antagonists using cyclodextrins and its derivatives, liposomes and biodegradable polymers and/or combinations of these systems and/or derivative products, which may be used for treating several pathologies, such as arterial hypertension, other cardiovascular diseases and their complications, wounds, burnings, erythemas, tumors, diabetes mellitus, among others.

Patent WO2007000036, Dos Santos et al. (2006) also describes the use of the Mas receptor coupled with G protein, agonists and antagonists, as modulator for apoptotic activity for the study prevention and treatment of diseases.

Nevertheless, the present invention is characterized by the use of the PEPTIDE $Ala^1$-Ang-(1-7) and/or related compounds, as for example, vascularprotective or cardioprotective agents in mammals. This invention also includes compositions containing the PEPTIDE $Ala^1$-Ang-(1-7) and/or related compounds and their use in methods for treating and preventing diseases and disorders. For example, such diseases include cardiovascular disturbances as primary or secondary hypertension, vascular-renal hypertension, atherosclerosis, ischemic and reperfusion injury, acute myocardial infarction, acute or chronic congestive myocardial insufficiency, left ventricular hypertrophy, vascular hypertrophy, primary and secondary hyperaldosteronism, diabetes, neuropathic diabetes, glomerulonephritis, scleroderma, glomerular sclerosis, renal insufficiency, therapies for organ transplants, diabetic retinopathy, nephropathies, angioplasties and erectile dysfunction.

The observation that PEPTIDE Des-[$Asp^1$]-[$Ala^1$]-Angiotensin-(1-7) ($Ala^1$-Ang-(1-7)) ($Ala^1$-$Arg^2$-$Val^3$-$Tyr^4$-$Ile^5$-$His^6$-$Pro^7$) produces vasodilation independently of the Mas receptor and the $AT_2$ receptor in the aorta rings of wild-type mice with deletion of the Mas receptor and mice with deletion of the $AT_2$ receptor is the most important feature of the present invention. Additionally, PEPTIDE Des-[$Asp^1$]-[$Ala^1$]-Angiotensin-(1-7) inhibits ACE.

PEPTIDE Des-[$Aps^1$]-[$Ala^1$]-Angiotensin-(1-7) ($Ala^1$-$Arg^2$-$Val^3$-$Tyr^4$-$Ile^5$-$His^6$-$Pro^7$) may be synthesized by using the solid-phase synthesis strategy, Fmoc/t-butyl, according to CHAN & WHITE, 2000 (CHAN, W. C & WHITE, P. D. Fmoc solid-phase peptide synthesis. A practical approach. Oxford University Press; 2000).

Des-[$Aps^1$]-[$Ala^1$]-Angiotensin-(1-7) may be optionally produced from decarboxylation of aspartic amino acid residue, which forms an alanine residue of PEPTIDE Angiotensin-(1-7) (Ang-(1-7)) ($Asp^1$-$Arg^2$-$Val^3$-$Tyr^4$-$Ile^5$-$His^6$-$Pro^7$) or from cleaving the phenylalanine residue of the N-terminal portion of PEPTIDE Des-[$Aps^1$]-[$Ala^1$]-Angiotensin II ($Ala^1$-$Arg^2$-$Val^3$-$Tyr^4$-$Ile^5$-$His^6$-$Pro^7$-$Phe^8$).

The $Ala^1$-Ang-(1-7) and/or related compounds are useful for treating and preventing vascular and cardiovascular diseases, but they are not limited to diseases such as cardiovascular disturbances, primary or secondary hypertension, vascular-renal hypertension, atherosclerosis, ischemic and reperfusion injury, acute myocardial infarction, acute or chronic congestive myocardial insufficiency, left ventricular hypertrophy, vascular hypertrophy, primary and secondary hyperaldosteronism, diabetes, neuropathic diabetes, glomerulonephritis, scleroderma, glomerular sclerosis, renal insufficiency, therapies for organ transplants, diabetic retinopathy, nephropathies, angioplasties and erectile dysfunction. The $Ala^1$-Ang-(1-7) and/or related compounds may be also used for treating and preventing diseases such as diabetic peripheral neuropathy, pains, cerebral vascular accident and cerebral ischemia. Therefore, $Ala^1$-Ang-(1-7) and/or related compounds may be also used as neuroprotective agents.

An embodiment of the present invention includes methods for treating and preventing vascular and cardiovascular diseases through the delivery of effective amounts of $Ala^1$-Ang-(1-7) and/or related compounds or pharmaceutical compositions containing $Ala^1$-Ang-(1-7) and/or related compounds.

Another embodiment of this invention is its use in methods or treating and preventing diseases related to endothelial dysfunction through the delivery of effective amounts of $Ala^1$-Ang-(1-7) and/or related compounds or pharmaceutical compositions containing $Ala^1$-Ang-(1-7) and/or related compounds.

It is also used in methods for treating and preventing neurological diseases through the delivery of effective amounts of $Ala^1$-Ang-(1-7) and/or related compounds or pharmaceutical compositions containing $Ala^1$-Ang-(1-7) and/or related compounds. Such neurological diseases include, for example, peripheral diabetic neuropathy, pains, cerebral vascular accident and cerebral ischemia.

The present invention can also be used for obtaining pharmaceutical compositions containing one or more compounds with $Ala^1$-Ang-(1-7) and/or related compounds as well as pharmaceutically and physiologically acceptable vehicles and/or excipients.

Producing this pharmaceutical composition requires the use of a combination containing $Ala^1$-Ang-(1-7) and/or its related compounds together with another compound for treating vascular, cardiovascular and neurologic diseases. For example, the $Ala^1$-Ang-(1-7) and/or its related compounds may be used combined with pharmaceuticals that are inhibitors of the angiotensin (ACE) converter enzyme for the treatment of diseases for which ACE inhibitors are conventionally used.

The present invention may be better understood by following its references, detailed description and illustrative examples, all of which are to be taken as its exemplified and non-limited incorporation.

EXAMPLE 1

The Vasodilating Effect of $Ala^1$-Ang-(1-7) Independent of the Mas Receptor

This example describes the vasodilating effect of $Ala^1$-Ang-(1-7), independently of the Mas receptor, on aorta rings of mice with genetic deletion of the Mas receptor (Mas-/-) and wild-type mice (Mas+/+) from two different lineages, C57/BI-6 and FVB/N.

The original rings of the descending thoracic aorta (2 mm), free from adipose tissue and connective tissue, were incubated in gasified solution (95% $O_2$ and 5% $CO_2$) of Krebs-Henseleit (mmol/L): NaCl 110.8, KCl 5.9, $NaHCO_3$ 25.0, $MgSO_4$ 1.07, $CaCl_2$ 2.49, $NaH_2PO_4$ 2.33 and glucose 11.51, under a temperature of 37° C. and a 0.5 g tension, being equilibrated for 1 hour. The functional presence of endothelium was tested by its relaxing capacity produced by acetylcholine [ACh] (10 µM) on vessels precontracted with fenilefrine (0.3 μM). Only the vessels showing relaxation above 70% of extended contraction produced by fenilefrine were taken into account. Data on mechanical activity were isometrically obtained by using an amplified strength transducer (Model TMB-4; World Precision Instruments, Inc. Sarasota, Fla., USA) and converted to digital signal (AD16JR; World Precision Instruments, Inc.). A specific software for data acquisition was also used (World Precision Instruments, Inc.).

The aorta rings of mice Mas−/− and Mas+/+ from both lineages (C57/Bl-6 and FVB/N) were precontracted to achieve the same tension level (approximately a 1.0 g tension) at a submaximum concentration of fenilefrine (0.1 μM). Ala$^1$-Ang-(1-7) and Ang-(1-7) were added in increasing and cumulative concentrations after stabilized contraction response to fenilefrine was achieved. The results are presented as ±E.P.M. mean values. The Two-way (ANOVA) test of variance analysis was used as a comparative method of curves, followed by the Bonferroni post-test for comparison of the dependent concentration curves obtained in the aorta rings. The vasodilating effects of Ala$^1$-Ang-(1-7) and Ang-(1-7) were expressed as a percentage of relaxation relative to the maximum contraction induced by fenilefrine. The statistical analyses were considered significant when the value of p was lower than 0.05.

Both PEPTIDES, Ala$^1$-Ang-(1-7) and Ang-(1-7), have produced vasorelaxation in aorta rings of Mas+/+ mice from both lineages (C57/Bl-6 and FVB/N). However, the vasodilating response of Ala$^1$-Ang-(1-7) was totally preserved in Mas−/− mice (from both lineages, C57/Bl-6 and FVB/N), and the absence of Ang-(1-7) (from both lineages, C57/Bl-6 and FVB/N) response was verified. These results show the vasodilating effect of Ala$^1$-Ang-(1-7), which is independent from the Mas receptor, as compared to the vasodilating effect of Ang-(1-7), which is Mas-dependent.

EXAMPLE 2

The Vasodilating Effect of Ala$^1$-Ang-(1-7) is Independent of the AT$_2$ Receptor This example describes the vasodilating effect of Ala$^1$-Ang-(1-7) and Ang-(1-7)—which is independent of the AT$_2$ receptor—on the aorta of mice with genetic deletion of AT$_2$ (AT$_2$−/−) receptor.

The original rings of the descending thoracic aorta (2 mm), free from adipose tissue and connective tissue, were incubated in gasified solution (95% O$_2$ and 5% CO$_2$) of Krebs-Henseleit (mmol/L): NaCl 110.8, KCl 5.9, NaHCO$_3$ 25.0, MgSO$_4$ 1.07, CaCl$_2$ 2.49, NaH$_2$PO$_4$ 2.33 and glucose 11.51, under a temperature of 37° C. and a 0.5 g tension, being equilibrated for 1 hour. The functional presence of endothelium was tested by its relaxing capacity produced by acetylcholine [ACh] (10 μM) on vessels precontracted with fenilefrine (0.3 μM). Only the vessels showing relaxation above 70% of extended contraction produced by fenilefrine were taken into account. Data on mechanical activity were isometrically obtained by using an amplified strength transducer (Model TMB-4; World Precision Instruments, Inc. Sarasota, Fla., USA) and converted to digital signal (AD16JR; World Precision Instruments, Inc.). A specific software for data acquisition was also used (World Precision Instruments, Inc.). A specific software for data acquisition was also used (World Precision Instruments, Inc.).

The aorta rings of AT$_2$−/− mice were precontracted (approx. 1.0 g of tension) with a felinefrine submaximum concentration (0.1 μM). Ala$^1$-Ang-(1-7) and Ang-(1-7) were added in increasing and cumulative concentrations after the contraction response to felinefrine has been stabilized. The results were shown as a ±E.P.M. mean. The Two-way (ANOVA) variance analysis was used as a comparative method of curves, which was followed by the Bonferroni post-test so as to compare the dependent-concentration curves obtained in the aorta rings. The vasodilating effects of Ala$^1$-Ang-(1-7) and Ang-(1-7) were expressed as a relaxation percentage relative to the maximum contraction induced by fenilefrine. The statistical analyses were considered significant when the value of p was lower than 0.05.

The vasodilating effects produced by Ala$^1$-Ang-(1-7) and Ang-(1-7) were preserved in the aorta rings of AT$_2$−/− mice. This proves that the vasodilating effects of Ala$^1$-Ang-(1-7) and Ang-(1-7) are receptor-independent.

EXAMPLE 3

The Vasodilating Effect of Ala$^1$-Ang-(1-7) is Endothelium-Dependent

This example describes the endothelium-dependence of the Ala$^1$-Ang-(1-7) vasorelaxing activity.

The original rings of the descending thoracic aorta (2 mm), free from adipose tissue and connective tissue, were incubated in gasified solution (95% O$_2$ and 5% CO$_2$) of Krebs-Henseleit (mmol/L): NaCl 110.8, KCl 5.9, NaHCO$_3$ 25.0, MgSO$_4$ 1.07, CaCl$_2$ 2.49, NaH$_2$PO$_4$ 2.33 and glucose 11.51, under a temperature of 37° C. and a 0.5 g tension, being equilibrated for 1 hour. The functional presence of endothelium was tested by its relaxing capacity produced by acetylcholine [ACh] (10 μM) on vessels precontracted with fenilefrine (0.3 μM). In accordance with experimental protocols for its absence, the endothelium was removed with a slight friction on the vessel internal surface. Only the vessels showing relaxation by acetylcholine above 70% of extended contraction produced by fenilefrine were taken into account. Data on mechanical activity were isometrically obtained by using an amplified strength transducer (Model TMB-4; World Precision Instruments, Inc. Sarasota, Fla., USA) and converted to digital signal (AD16JR; World Precision Instruments, Inc.). A specific software for data acquisition was also used (World Precision Instruments, Inc.).

The Ala$^1$-Ang-(1-7) vasorelaxing activity was measured in vessels (Mas+/+ and Mas−/−, of lineages C57/Bl-6 and FVB/N) in the presence or absence of precontracted functional endothelium (with approximately a 1.0 g tension) and a submaximum concentration of fenilefrine (0.1 μM). Ala$^1$-Ang-(1-7) was added in increasing and cumulative concentrations after stabilization of contraction response to felinefrine had been achieved. The results were presented as a ±E.P.M. mean. The two-way (ANOVA) variance analysis was used as a comparative method of curves, which was followed by the Bonferroni post-test so as to compare the dependent-concentration curves obtained in the aorta rings. The vasodilating effects of Ala$^1$-Ang-(1-7) and Ang-(1-7) were expressed as a relaxation percentage relative to the maximum contraction induced by fenilefrine. The statistical analyses were considered significant when the value of p was lower than 0.05.

The vasodilating effect of Ala$^1$-Ang-(1-7) was abolished in vessels not presenting functional endothelium (FIGS. 1-4). These results show that the vasodilating effect produced by Ala$^1$-Ang-(1-7) is endothelium-dependent.

EXAMPLE 4

Ala¹-Ang-(1-7) Inhibits the Angiotensin Converter Enzyme

This example describes the inhibiting activity of the angiotensin converter enzyme (ACE) produced by Ala¹-Ang-(1-7).

The plasmatic activity of ACE was measured by the fluorimetric method using Hip-His-Leu as substrate, as previously described (Santos, R. A. S. et al., Hypertension, 7:244-52, (1985)). Plasma aliquots (10 µL) of Wistar rats were incubated with a 500 mL solution containing a 1 mM substrate (Hip-His-Leu) and 0.4 M of sodium borate, 0.9 M NaCl (pH=8.3) for 15 minutes at 37° C. The reaction was halted by adding 1.2 mL of NaOH at 0.34 M and 100 mL of orthoftaldehyde (20 mg/mL in methanol). After 10 minutes at environment temperature, 200 mL of HCl at 3 N was added. Later on, after a 5-minute 800×g centrifugation, the floating solution fluorescence was measured (a 365 nm excitation and a 495 nm emission). The blank was prepared by inverting the addition order of plasma and NaOH. A 0.5 to 20 nmol curve, containing the product (His-Leu) resulting of the substrate break (Hip-His-Leu) by ACE plasmatic activity, was prepared in each assay. In order to test the inhibition effect of ACE by the PEPTIDEs Ang-(1-7) and Ala¹-Ang-(1-7), $3.3 \times 10^{-7}$ or $3.3 \times 10^{-6}$ M of each PEPTIDE was added before the plasma addition. The assay specificity was demonstrated by a 98% inhibition of the ACE activity with the use of 5 mM of enalaprilate. The percentage of enzymatic activity inhibition was estimated in function of the maximum activity obtained.

The PEPTIDEs Ang-(1-7) and Ala¹-Ang-(1-7) have inhibited the ACE activity, although the inhibiting effect of Ala¹-Ang-(1-7) ($3.3 \times 10^{-7}$ M: 76.3% of ACE inhibition, $3.3 \times 10^{-6}$ M: 98.3% of inhibition) was higher than that of Ang-(1-7) ($3.3 \times 10^{-7}$ M: 42.4% of ACE inhibition, $3.3 \times 10^{-6}$ M: 85.8% of inhibition).

EXAMPLE 5

Preparing and Characterizing the Inclusion Complexes of Peptide Ala¹-Ang-(1-7) in Cyclodextrins Preparation of the inclusion complex between β-cyclodextrin and its derivatives and Ala¹-Ang-(1-7) and its related compounds.

The preparation is accomplished in equimolar proportions of β-cyclodextrin and its derivatives and Ala¹-Ang-(1-7) and its related compounds in aqueous solutions. The solution mixture is constantly agitated up to the complete β-cyclodextrin dissolution.

Later on the combination is frozen at the liquid nitrogen temperature and submitted to lyophilization for 24 hours. The solid thus obtained was characterized by means of the physico-chemical techniques of analysis. The technique used, which provided important characteristics of the host/guest interaction, was that of fluorescence and spectroscopy of absorption in the ultraviolet-visible region.

The absorption and biological stability tests were carried out with solutions of the peptide-cyclodextrin inclusion complex. Devices of controlled peptide release were prepared as well as those of their peptide-cyclodextrin inclusion complexes.

Therefore, the peptide Ala¹-Ang-(1-7) and its related compounds, combined with cyclodextrin, results in an oral or systemic formulation with longer effect duration.

SEQUENCE LISTING

Figure 1:
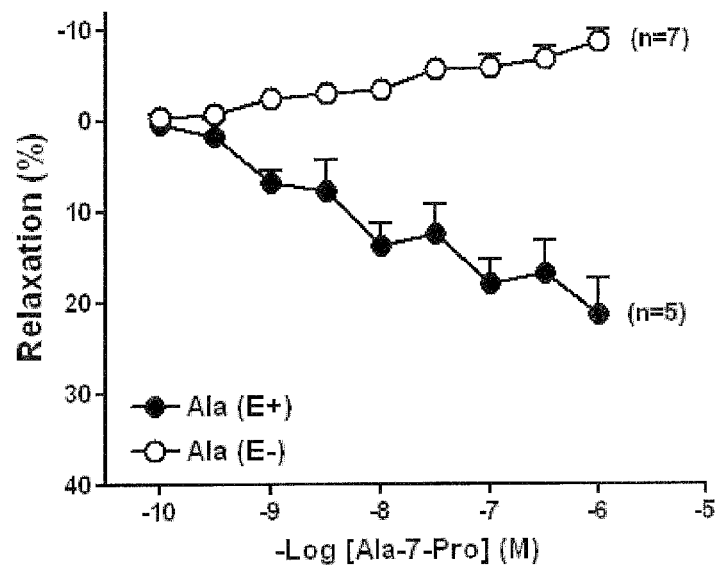
FIG. 1 shows the endothelium dependence for the vasodilating effect of Ala¹-Ang-(1-7) and Ang-(1-7) in aorta rings of Mas −/−mice of FVB/N lineage. Each dot represents the +E.P.M. mean.
Figure 2:
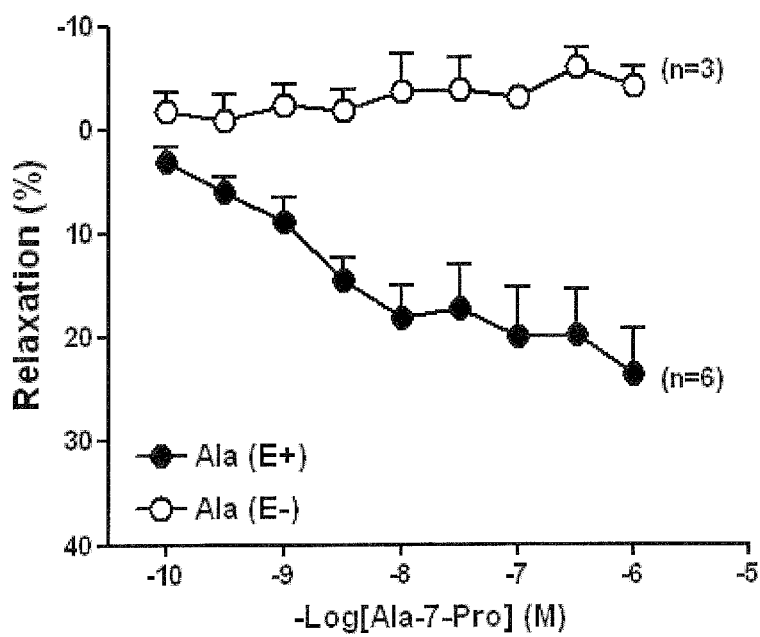
FIG. 2 shows the endothelium dependence for the vasodilating effect of Ala¹-Ang-(1-7) and Ang-(1-7) in aorta rings of Mas +/+ mice of FVB/N lineage. Each dot represents the +E.P.M. mean.
Figure 3:
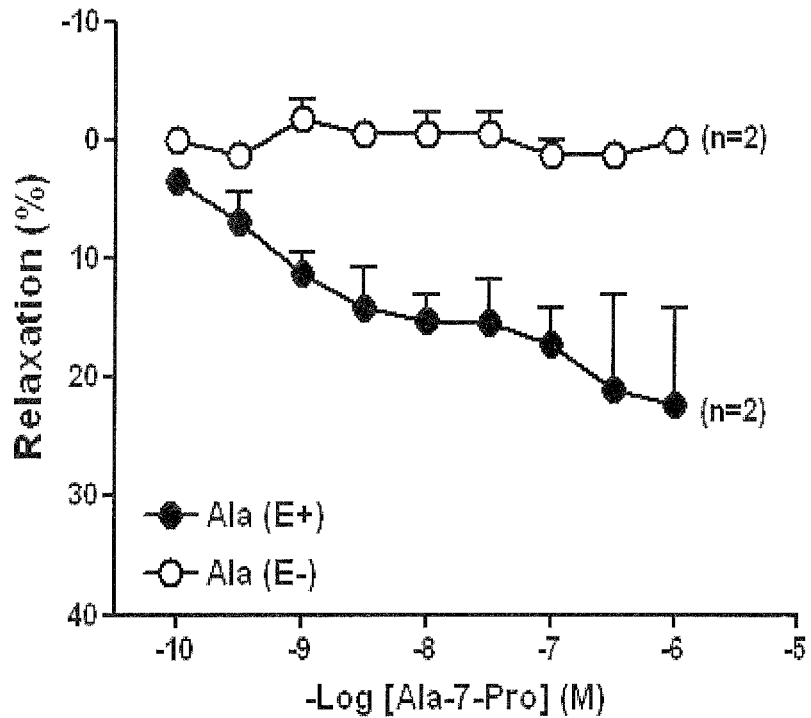
FIG. 3 shows the endothelium dependence for the vasodilating effect of Ala¹-Ang-(1-7) and Ang-(1-7) in aorta rings of Mas −/−mice of C57/BL-6 lineage. Each dot represents the +E.P.M. mean.
Figure 4:
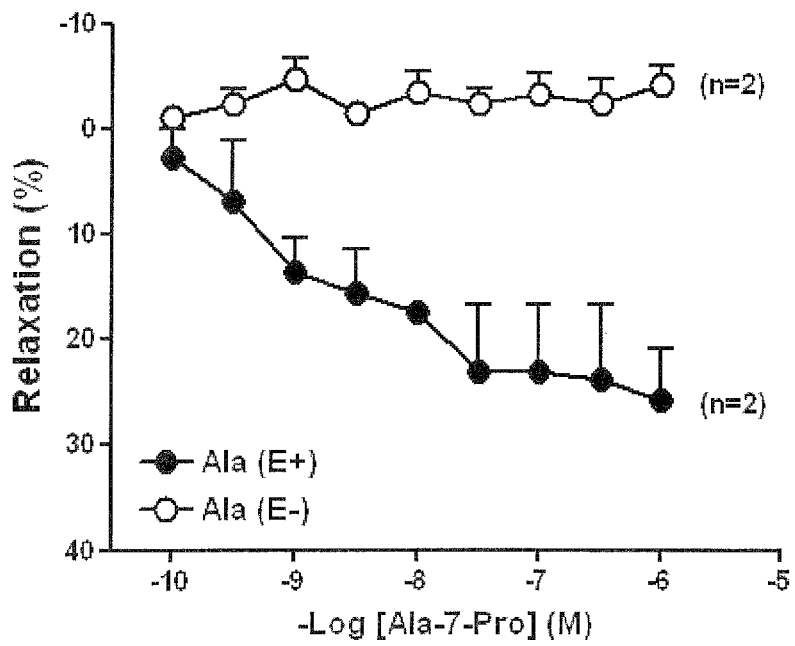
FIG. 4 shows the endothelium dependence for the vasodilating effect of Ala¹-Ang-(1-7) and Ang-(1-7) in aorta rings of Mas+/+ mice of C57/BL-6 lineage. Each dot represents the +E.P.M. mean.
Figure 5:
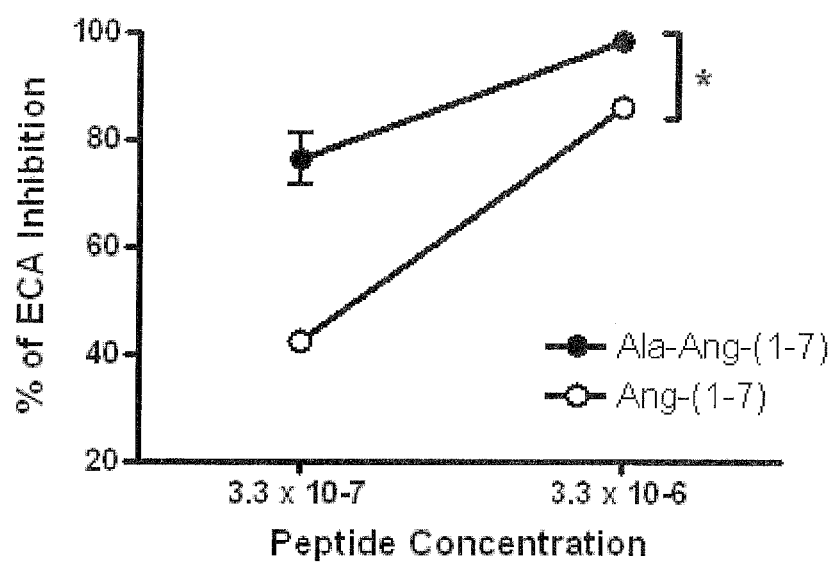
FIG. 5 shows the inhibiting activity of ACE by PEPTIDEs Ala¹-Ang-(1-7) and Ang-(1-7). Each dot represents the ±E.P.M. mean.

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Ala Arg Val Tyr Ile His Pro
                5
```

The invention claimed is:

1. A peptide Des-[Asp$^1$]-[Ala$^1$]-Angiotensin-(1-7) consisting of the amino acid sequence SEQ ID NO: 1.

2. A pharmaceutical composition comprising the peptide Des-[Asp$^1$]-[Ala$^1$]-Angiotensin-(1-7) as defined in claim 1, in pharmaceutically and physiologically acceptable carriers and/or excipients.

3. The pharmaceutical composition according to claim 2, which is administered by an oral, intramuscular, intravenous, subcutaneous, topical, or a transdermal route or a device to be implanted or injected.

4. The pharmaceutical composition according to claim 2, which is included in a controlled release system comprising a cyclodextrin, biodegradable polymer, mucoadhesive polymer, gel, or liposome.

5. The peptide according to claim 1, which is formulated for treatment of a vascular or cardiovascular disease in a human or other mammal.

6. The peptide according to claim 1, which is formulated for treatment of a neurological disease or disorder in a human or other mammal.

7. The peptide according to claim 1, which is formulated for treatment of a renal, endocrinal, reproductive, dermatological, neoplastic, or blood disease or disorder in a human or other mammal.

8. A method for treatment of disease, comprising administration of an effective amount of Ala$^1$-Angiotensin-(1-7) and/or related components as defined in claim 1 or of a pharmaceutical composition thereof for treating a disease selected from the group consisting of cardiovascular, renal, endocrinal, reproductive, dermatological, neoplastic, blood, and cerebral diseases.

9. The method according to claim 8, which is administered by an oral, intramuscular, intravenous, subcutaneous, topical, or transdermal route or a device to be implanted or injected.

10. The method according to claim 8, wherein a controlled release system comprising at least cyclodextrin, biodegradable polymer, mucoadhesive polymer, gel, or liposome is also administered.

11. A method for treatment of a vascular or cardiovascular disease or disorder, comprising administration of an effective amount of Ala$^1$-Angiotensin-(1-7) as defined in claim 1 or of a pharmaceutical composition thereof to a patient in need thereof.

12. The method according to claim 11, the disease or disorder is selected from the group consisting of endothelium dysfunction, atherosclerosis, ischemic and reperfusion injury, acute myocardial infarction, high blood pressure, primary and secondary arterial hypertension, chronic and acute congestive cardiac insufficiency, left ventricular hypertrophy, vascular hypertrophy, primary and secondary hyperaldosteronism, diabetes, diabetic nephropathy, glomerulonephritis, scleroderma, glomerular sclerosis, renal insufficiency, therapies for kidney transplants or diabetic retinopathy, and angioplasty.

13. The method according to claim 11, which is administered by oral, intramuscular, intravenous, subcutaneous, topical, or transdermal route or a device to be implanted or injected.

14. The method according to claim 11, wherein a controlled release system comprising at least cyclodextrin, biodegradable polymer, mucoadhesive polymer, gel, or liposome is also administered.

15. A method for treatment of a neurological disease or disorder, comprising administration of an effective amount of Ala$^1$-Angiotensin-(1-7) as defined in claim 1 or of a pharmaceutical composition thereof to a patient in need thereof.

16. The method according to claim 15, wherein the disease or disorder is selected from the group consisting of peripheral diabetic neuropathy, pain, cerebral vascular accident, and cerebral ischemia.

17. The method according to claim 15, which is administered by oral, intramuscular, intravenous, subcutaneous, topical, or transdermal route or a device to be implanted or injected.

18. The method according to claim 15, wherein a controlled release system comprising at least cyclodextrin, biodegradable polymer, mucoadhesive polymer, gel, or liposome is also administered.

19. A process for making a pharmaceutical composition according to claim 2, comprising formulating the peptide Des-[Asp$^1$]-[Ala$^1$]-Angiotensin-(1-7) in at least a pharmaceutically and physiologically acceptable carrier and/or excipient, isolated or combined, or even associated at least to another pharmaceutically active principle to make the pharmaceutical composition.

* * * * *